United States Patent
Aggarwal et al.

(10) Patent No.: US 11,331,266 B1
(45) Date of Patent: May 17, 2022

(54) ANTIOXIDANT FREE, NOREPINEPHRINE BITARTRATE INJECTION IN AMBER GLASS VIALS

(71) Applicant: Medefil, Inc., Glendale Heights, IL (US)

(72) Inventors: Pradeep Aggarwal, Oak Brook, IL (US); Lincoln W. Maina, Schaumburg, IL (US); Sunil Potdar, Schaumburg, IL (US); Ravinder Malhotra, Long Grove, IL (US); Venugopal Chenna, Vernon Hills, IL (US); Sandeep Pallerla, Hoffman Estates, IL (US); NagaBhuvan Kumar Nandipati, Schaumburg, IL (US)

(73) Assignee: Medefil, Inc., Glendale Heights, IL (US)

( * ) Notice: Subject to any disclaimer, the term of this patent is extended or adjusted under 35 U.S.C. 154(b) by 0 days.

(21) Appl. No.: 17/083,890

(22) Filed: Oct. 29, 2020

(51) Int. Cl.
| | |
|---|---|
| *A61K 9/00* | (2006.01) |
| *A61K 31/137* | (2006.01) |
| *A61K 9/08* | (2006.01) |
| *A61K 47/26* | (2006.01) |
| *A61K 47/02* | (2006.01) |

(52) U.S. Cl.
CPC ............. *A61K 9/0019* (2013.01); *A61K 9/08* (2013.01); *A61K 31/137* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 9,119,876 B1 | 9/2015 | Kannan et al. | |
| 9,187,779 B2 | 11/2015 | Plumere et al. | |
| 9,295,657 B1 | 3/2016 | Kannan et al. | |
| 9,877,935 B2 | 1/2018 | Rakesh et al. | |
| 10,226,436 B2 | 3/2019 | Puri et al. | |
| 10,251,848 B2* | 4/2019 | Mitidieri | A61K 9/0019 |
| 10,420,735 B2 | 9/2019 | Hingorani et al. | |
| 2016/0058715 A1* | 3/2016 | Rakesh | A61K 31/00 514/653 |
| 2018/0214394 A1 | 8/2018 | Puri et al. | |

FOREIGN PATENT DOCUMENTS

WO 2015128418 A1 9/2015

OTHER PUBLICATIONS

Lanigan, R.S. et al, "Final Report on the Safety Assessment of BHT," Int. J. Toxicol. 2002; 21 Suppl 2:19-94.
Levophed Package Insert, Hospira, Inc., Revised Mar. 2018 (9 pages).
Baxter Norepinephrine Package Insert, Reference ID: 4732174, Jan. 2021 (9 pages).

* cited by examiner

*Primary Examiner* — Robert A Wax
*Assistant Examiner* — Quanglong N Truong
(74) *Attorney, Agent, or Firm* — Taft Stettinius & Hollister LLP; Joseph M. Bennett-Paris

(57) ABSTRACT

The application provides pharmaceutical compositions comprising stable concentrated solutions of antioxidant free norepinephrine bitartrate for injection dispensed in glass containers and methods of providing such solutions to a subject.

21 Claims, No Drawings

ANTIOXIDANT FREE, NOREPINEPHRINE BITARTRATE INJECTION IN AMBER GLASS VIALS

FIELD OF THE INVENTION

The present invention relates to the stability of concentrated solution of antioxidant free norepinephrine bitartrate for injection dispensed in amber glass containers and methods of providing such solutions to a subject.

BACKGROUND OF THE INVENTION

Norepinephrine (sometimes referred to as 1-arterenol/Levarterenol or 1-norepinephrine) is a sympathomimetic amine often used during cardiopulmonary resuscitation (CPR) and in treatment of cardiac arrest and profound hypotension. Norepinephrine is also used for blood pressure control in certain acute hypotensive states, including for example sympathectomy, poliomyelitis, pheochromocytomectomy, spinal anesthesia, myocardial infarction, blood transfusion, and septicemia.

Norepinephrine is currently marketed by Hospira Inc. as LEVOPHED®, as a concentrate; 1 mg/mL norepinephrine bitartrate formulation with sodium metabisulfite as an antioxidant. LEVOPHED® is to be administered by intravenous infusion following dilution with dextrose or dextrose with sodium chloride injection.

Norepinephrine Bitartrate Injection, USP is also marketed as Claris® by Baxter as an antioxidant-free norepinephrine concentrate (free of sodium metabisulfite) and packaged under nitrogen in glass ampules.

Ready-to-inject, storage stable, antioxidant free norepinephrine compositions and methods of manufacturing such compositions are also known in the prior art. For example, U.S. Pat. No. 10,226,436 assigned to Nevakar, Inc. discloses a particular antioxidant free sterilizable/autoclavable ready-to-inject norepinephrine compositions comprising an aqueous acidic buffer having a pH range of between 3.7-4.3 that includes a chelating agent and a pharmaceutically acceptable salt. The resulting compositions were shown to exhibit low isomerization (<10%) and less than 5% degradation of total norepinephrine.

U.S. Pat. No. 9,877,935 assigned to Sun Pharmaceutical Industries, Ltd. discloses a ready-to-administer parenteral dosage form in an aqueous solution comprising norepinephrine, antioxidant which is not a sulfite antioxidant. The patentees utilized instead, butylated hydroxyl anisole as an antioxidant. However, while generally deemed safe for topical and cosmetic use, butylated hydroxyl anisole was shown to produce some renal and hepatic damage. See for example Lanigan, R. S. et al, "Final Report on the Safety Assessment of BHT," Int. J. Toxicol. 2002; 21 Suppl 2:19-94 and the citations therein.

LEVOPHED® contains an antioxidant, sodium metabisulfite, and the package insert carries a warning label that sulfite may cause allergic type reactions including anaphylactic shock and life threatening or less severe asthmatic episodes in susceptible people.

LEVOPHED® is also available in only 4 mL fill volume containing 4 mg norepinephrine. In many cases, clinicians need to combine 2 to 4 vials to achieve desired dose of norepinephrine to meet patient clinical need. This inherently adds to additional risk of diluting multiple vials into a bag and chances of contamination U.S. Pat. No. 10,251,848 (originally published as WO 2015/128418; assigned to Sintetica S.A.) discloses yet another attempt to provide ready-to-administer norepinephrine formulations with increased storage stability and reduced risk of human error. The patentees disclose that the pH of the injectable solution was reduced to between 3.2 and 3.6 with a high dose of 40-200 µg/ml norepinephrine. It is disclosed that while such formulations exhibited reduced degradation as compared to higher pH (3.7-4.5) formulations, significant discomfort can occur at the injection site. Worse yet, at the pH used, norepinephrine degradation by isomerization was observed to occur relatively quickly as disclosed in U.S. Pat. No. 10,226,436.

Epinephrine is a related molecule to norepinephrine differing from norepinephrine by presence of a methyl group on the nitrogen atom. Epinephrine is a non-selective alpha and beta-adrenergic agonist indicated to increase mean arterial blood pressure in adult patients with hypotension associated with septic shock, for emergency treatment of allergic reactions (type 1) including anaphylaxis, and for induction and maintenance of mydriasis during intraocular surgery.

Pharmaceutical compositions comprising epinephrine, methods of administration, and methods of making these compositions are well known. For example, U.S. Pat. No. 9,119,876 assigned to Par Pharmaceutical Inc. The patentees disclose epinephrine compositions that include a pH raising agent, an antioxidant, a transitional metal complexing agent, a pH lowering agent, a tonicity regulating agent, with optional preservatives and a solvent. Related U.S. Pat. No. 9,295,657 assigned to Par Pharmaceutical Inc. discloses epinephrine compositions with 17% or less of impurities such as epinephrine sulfonic acid impurity (ESA).

Pharmaceutical compositions of epinephrine which are more potent and less toxic than existing pharmaceutical formulations, along with methods of producing and using the pharmaceutical compositions have been patented. These compositions are provided in prefilled syringes used in treating patients with continuous intravenous infusion instead of bolus administration.

What is needed is a stable no-additives pharmaceutical formulation of norepinephrine injection available in commonly used, providers-preferred, glass vials with varying amount of drug for ease and safety of intravenous dilutions.

SUMMARY OF THE INVENTION

The present application provides compositions of stable, quality norepinephrine pharmaceutical composition without allergy causing sulfites affecting mostly neonates and adult population with sulfite allergies.

Furthermore, unlike the currently available norepinephrine compositions which are provided in an ampoule, the norepinephrine pharmaceutical composition of the current invention is packaged in a container closure system which provides increased storage stability of a norepinephrine concentrate solution which is antioxidant free dispensed in amber glass containers and methods of providing such solutions. The glass vials eliminate the possibility of generating life threatening glass particles as in the case of ampoules cutting.

Other embodiments of the current invention include glass vials with additional fill volumes of 8 mL and 16 mL containing 8 mg and 16 mg norepinephrine base respectively. These additional fill volumes will avoid any dilution errors when larger doses of norepinephrine are required for the patients to meet clinical end point. At present, pharmacist needs to combine multiple 4 mL vials containing 4 mg norepinephrine base to make 8 mg (combining 2 vials) and 16 mg (combining 4 vials) to make desired strength of the IV diluted solutions. The vials of the current inventions will thus avoid possible dilution errors and contamination which can occur while opening multiple vials.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

DETAILED DESCRIPTION OF THE INVENTION

Norepinephrine degradation usually follows three major pathways: oxidation, complexation by sulfonation and racemization. Norepinephrine concentrate solutions similar to LEVOPHED® try to curb oxidative degradation by adding an antioxidant, usually sodium metabisulfite. While the antioxidant may scavenge the oxygen and thereby curb the oxidation pathway, it forces degradation via sulfonation. The degradant is a new sulfonated compound of unknown activity and toxicity. In addition, norepinephrine is also known to undergo other minor degradations caused by and not limited to light, alkaline and acidic conditions. The current invention provides a formulation that is stable at acidic pH and the use of amber vials protects the product from light oxidation.

By providing stable pharmaceutical solution compositions with a long product shelf life, the current invention eliminates entirely the sulfonation pathway and minimizes degradation via oxidation while maintaining comparable levels of racemization to the formulation with the antioxidant.

Yet another advantage of the current invention is providing container closure systems of glass vials that eliminate the potential for glass particulates, microbial contamination and reduced potential injury risks to the providers while breaking a traditional ampoule glass container. The main disadvantage of ampules is that they require glass breakage and filtration of glass particulates. These steps thereby introduce the risk of microbial contamination.

In addition, to provide stability to the formulations of the current invention, the formulation is compounded with low levels of dissolved oxygen (0-1 ppm) and the compositions are packaged under controlled oxygen environments. As a non-limiting example, formulations are provided with dissolved oxygen levels in the formulation to be less than 2 ppm, and the headspace of the packaging container to contain between 0.5% to 8% oxygen headspace and more specifically 0.5% to 2% oxygen headspace. By replacing the headspace with nitrogen, argon or other pharmaceutically inert gases as well as under vacuum technology, the formulations remain stable throughout the recommended shelf life. In certain embodiments, the stable injectable norepinephrine solutions are prepared by sparging with inert gases to achieve dissolved oxygen levels of about 0 to about 2 ppm during compounding. In other embodiments, the stable injectable norepinephrine solutions are prepared by sparging with inert gases to achieve dissolved oxygen levels of about 0 to about 5 ppm when measured up to three months or more following packaging.

Another advantage of the current invention is additional fill volumes of 8 mL and 16 mL containing 8 mg and 16 mg of the norepinephrine base respectively. These additional fill volumes will avoid any dilution errors when higher amount of norepinephrine is required for the patients to meet clinical end point. At present, pharmacists need to combine multiple 4 mL vials containing 4 mg norepinephrine base to make 8 mg (combination of 2 vials), 16 mg (combination of 4 vials) and up to 68 mg (combination of 17 vials) to make occasional much larger doses necessary if the patient remains hypotensive. These additional codes will avoid possible dilution errors and reduce the number of vials required, thereby minimizing the possibility of microbial contamination while opening multiple vials. Consequently, it also significantly reduces preparation time which is critical due to the drug product's indications and usage.

In the specification and in the claims, the terms "including" and "comprising" are open-ended terms and should be interpreted to mean "including, but not limited to . . . " These terms encompass the more restrictive terms "consisting essentially of" and "consisting of".

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As used herein, the term "norepinephrine" refers to a the bitartrate salt of norepinephrine, norepinephrine bitartrate or (−)-α-(aminomethyl)-3,4-dihydroxybenzyl alcohol tartrate (1:1) (salt) monohydrate. Other pharmaceutically acceptable salts of norepinephrine may include, but is not limited to, inorganic acids such as hydrochloric acid, hydrobromic acid, sulfuric acid, nitric acid, phosphoric acid, and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid.

A "subject" or "patient" is a human, a non-human mammal or a non-human animal. Although the animal subject may be human, the compounds and compositions of the invention have application in veterinary medicine as well, e.g., for the treatment of domesticated species such as canine, feline and various other pets; farm animal species such as bovine, equine, ovine, caprine, porcine, etc.; wild animals, e.g. in the wild or in a zoological garden; and avian species such as chickens, turkeys, quail, songbirds, etc.

The term "purified" as used herein refers to material that has been isolated under conditions that reduce or eliminate the presence of unrelated materials, i.e. contaminants, including native materials from which the material is obtained. As used herein, the term "substantially free" is used operationally, in the context of analytic testing of the material. Preferably, purified material substantially free of contaminants is at least 95% pure, more preferably at least 97% pure, yet more preferably at least 99% pure. Purity can be evaluated for example by chromatography or any other methods known in the art. In particular embodiments purified means that the level of contaminants is below a level acceptable to regulatory authorities for safe administration to a human or a non-human animal.

The term "pharmaceutically acceptable," when used in connection with the pharmaceutical compositions of the application, refers to molecular entities and compositions that are physiologically tolerable, and do not typically produce untoward reactions when administered to a human. Preferably as used herein, the term "pharmaceutically acceptable" means approved by a regulatory agency of the Federal or state government or listed in the U.S. Pharmacopeia or other generally recognized pharmacopeia for use in animals, and more particularly in humans. The term "carrier" refers to a diluent, excipient, dispersing agent or vehicle with which the composition is administered. Such pharmaceutical carriers can be sterile liquids, such as water and oils. For example water, aqueous solutions, saline solutions or aqueous glycerol solutions can be employed as carriers, particularly for injectable solutions. Suitable pharmaceutical carriers are described in, for example, "Remington's Pharmaceutical Sciences" by Philip P. Gerbino, 22nd Edition). Aqueous solutions are those in which water is the solvent. The term "pharmaceutical composition" as used in accordance with the present application relates to compositions that can be formulated in any conventional manner using one or more pharmaceutically acceptable carriers or excipients.

In a preferred embodiment, the stable norepinephrine pharmaceutical compositions are diluted in saline. In alternate embodiments, the compositions of the current invention are diluted with dextrose or dextrose in saline containing mixtures.

The term "dosage" is intended to encompass a formulation expressed in terms of μg/kg/day, μg/kg/hr., mg/kg/day or mg/kg/hr. The dosage is the amount of an ingredient administered in accordance with a particular dosage regimen. A "dose" is an amount of an agent administered to a mammal in a unit volume or mass, e.g., an absolute unit dose expressed in mg or μg of the agent. The dose depends on the concentration of the agent in the formulation, e.g. in moles per liter (M), mass per volume (m/v) or mass per mass (m/m). The two terms are closely related, as a particular dosage results from the regimen of administration of a dose or doses of the formulation. The particular meaning in any case will be apparent from context.

The terms "therapeutically effective dose," "effective amount", and "therapeutically effective amount" refer to an amount sufficient to produce the desired effect. In the non-limiting embodiments, a "therapeutically effective dose" means an amount sufficient to reduce by at least about 15%, preferably by at least 50%, more preferably by at least 90% and most preferably prevent a clinically significant deficit in the activity, function and response of the host. Alternatively, a therapeutically effective amount is sufficient to cause an improvement in a clinically significant condition in the recipient. These parameters will depend on the severity of the condition being treated, other actions that are being implemented such as administration of other compounds, the weight, age and sex of the subject, and other criteria, which can be readily determined according to good medical practice by those of skill in the art.

In other non-limiting embodiments, a therapeutic response may be any response that a user (for example a clinician or other medical professional), will recognize as an effective response to the therapy. Thus, a therapeutic response will generally be an induction of a desired effect, such as, for example, increasing blood pressure in order to treat hypotension.

The terms "about" or "approximately" as used herein mean within an acceptable error range for the particular value as determined by one of ordinary skill in the art, which will depend in part on how the value is measured or determined, i.e. the limitations of the measurement system. For example, "about" can mean within 3 or more than 3 standard deviations, per the practice in the art. Alternatively, particularly with respect to biological systems or processes, the term can mean within an order of magnitude, preferably within 5-fold and more preferably within 2-fold, of a value.

The compositions of the application may be formulated as pharmaceutical compositions by admixture with a pharmaceutically acceptable carrier or excipient. In certain non-limiting embodiments, the compounds or compositions are provided in a therapeutically effective amount to an animal such as a mammal, preferably a human, in need of treatment therewith for increasing blood pressure, for example during cardio-pulmonary resuscitation (CPR), and in the treatment of cardiac arrest and profound hypotension. The compositions can also be used for blood pressure control in certain acute hypotensive states, including for example sympathectomy, poliomyelitis, pheochromocytomectomy, spinal anesthesia, myocardial infarction, blood transfusion, and septicemia.

In certain non-limiting embodiments, norepinephrine is formulated as a composition, wherein the norepinephrine is the only therapeutically active ingredient present in the composition. In another non-limiting embodiment, norepinephrine is formulated as a composition, wherein the norepinephrine is formulated in combination with at least one or more therapeutically active ingredient. In other non-limiting embodiments, the norepinephrine is administered to a subject in conjunction with at least one or more other therapeutically active ingredients. Such administration may be prior to, concomitant with or consecutive to the administration of the at least one other therapeutically active ingredient. The formulation is preferably suitable for parenteral administration, including but not limited to, intravenous, subcutaneous, intramuscular and intraperitoneal administration. However, formulations suitable for other routes of administration such as oral, intranasal, mucosal or transdermal are also contemplated.

The pharmaceutical formulations suitable for injectable use, such as, for example, intravenous, subcutaneous, intramuscular and intraperitoneal administration include sterile aqueous solutions or dispersions. In all cases, the form can be sterile and can be fluid to the extent that easy syringeability exists. It can be stable under the conditions of manufacture and storage and can be preserved against the contaminating action of microorganisms such as bacteria and fungi.

A composition or solution that "is stable" exhibits no more than a 5% decrease in the concentration of norepinephrine, or exhibits no more than a 4% decrease in the norepinephrine concentration, or exhibits no more than a 3% decrease in the norepinephrine concentration, or exhibits no more than a 2% decrease in the norepinephrine concentration, or exhibits no more than a 1% decrease in the norepinephrine concentration, or exhibits no more than a 0.5% decrease in the norepinephrine concentration at the indicated time span. Methods of testing stability under less than optimal conditions such as elevated temperature to predict longer term stability are known in the art. Accelerated stability conditions allow predictions of composition stability at durations at least as long as 24 months.

More specifically, with respect to stability it is contemplated that the storage condition is over at least three months at 40° C. and 75% (+/−5) relative humidity, that equal or no more than 15% of the R-isomer form of norepinephrine will isomerize to the S-isomer, or no more than 10% of the R-isomer form of norepinephrine will isomerize to the S-isomer, or no more than 8% of the R-isomer form of norepinephrine will isomerize to the S-isomer and the total norepinephrine will degrade to other degradation products no more than 5%, or the total norepinephrine will degrade to other degradation products no more than 2%.

Where desired, contemplated compositions have a dissolved oxygen concentration of equal or less than 1 ppm (e.g., by formulating the liquid parenteral composition using deoxygenated water), and/or or by packaging the composition together with a (preferably metal free) oxygen scavenger. Packaging may further make use of a container that is configured (e.g., aluminized or otherwise treated) to reduce light-mediated oxidation of the norepinephrine.

It is contemplated that although norepinephrine bitartrate has a high aqueous solubility, the carrier can also be a solvent or dispersion medium containing for example, water, saline, ethanol, polyol (for example glycerol, propylene glycol, polyethylene glycol and the like), suitable mixtures thereof and oils. The solubility of the carrier will depend upon the particular salt form of norepinephrine being used. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example parabens, chlorobutanol, phenol benzyl alcohol, sorbic acid and the like.

In various embodiments, the formulation may comprise a pharmaceutically acceptable excipient. As used herein, the term "stabilizer" refers to a compound optionally used in various embodiments to avoid the need for sulfite salts and increase storage life. Non-limiting examples may be a buffer or a non-ionic detergent.

Buffer systems for use in the present embodiments may include citrate, acetate, bicarbonate and phosphate buffers. Suitable buffers are generally buffers that stabilize the pH of the contemplated liquid formulations in an acidic pH range and will therefore include glycine buffers, citrate buffers, citrate/phosphate buffers, acetate buffers, etc. However, the inventors have further discovered that where the norepinephrine is provided as the norepinephrine bitartrate salt, a buffer can advantageously be omitted and the pH can be adjusted with suitable acid and/or base as is well known in the art. Notably, in some current embodiments there is no pH adjustment and the bitartrate appeared to act as a weak buffer in the stability range for the norepinephrine as is shown in more detail below. Most typically the pH of the formulation will be less than 5.0 and more typically less than 4.5, and most typically less than 4.3, but higher than 3.0, more typically about 3.5. For example, suitable buffers will have a pH in the range of between 3.7 and 4.3, or between 3.7 and 4.0, or between 3.8 and 4.1, or between 3.9 and 4.2, or between 4.0 and 4.2. Notably, such pH range provided remarkable stability for low concentrations of norepinephrine, especially when in combination with a chelator and a salt. While not limiting to the inventive subject matter, the buffer strength is typically relatively low, for example, equal or less than 100 mM, and more typically equal or less than 50 mM, and most typically between 5 mM and 20 mM (e.g., 10 mM).

With respect to suitable salts it is contemplated that the salt is a pharmaceutically acceptable salt that can be used to increase tonicity. Therefore, pharmaceutically acceptable salts are contemplated, and especially NaCl, at a concentration of at least 0.6 wt %, or at least 0.7 wt %, or at least 0.8 wt %, or at least 0.9 wt %. For example, suitable salt concentrations are between 0.6 wt % and 1.2 wt %. Depending on the particular salt concentration, additional tonicity agents may be added and suitable tonicity agents include glycerol, thioglycerol, mannitol, lactose, and dextrose. The amount of tonicity adjusting agent used can be adjusted to obtain osmolality of the formulations in the range of 260 to 340 mOsm/kg. An osmometer can be used to check and adjust the amount of tonicity adjusting agent to be added to obtain the desired osmolality.

Moreover, in further contemplated aspects, the formulation will also include one or more chelating agents, and particularly metal ion chelators. For example, suitable chelators include various bicarboxylic acids, tricarboxylic acids, and aminopolycarboxylic acids such as ethylenediaminetetraacetic acid (EDTA), ethylene glycol-bis(β-aminoethyl ether)-N,N,N',N'-tetraacetic acid (EGTA), and penta(carboxymethyl)diethylenetriamine (DTPA), and salts and hydrates thereof. While not limiting to the inventive subject matter, it is contemplated that the metal ion chelators will slow down both the baseline and metal ion-stimulated autoxidation of norepinephrine. The desirable effect of the chelators is typically observable at relatively low concentrations of the chelators. For example, reduction of the baseline and metal ion-stimulated autoxidation of norepinephrine was observed at chelator concentrations of between 1 μg/ml and 10 μg/ml, and between 10 μg/ml and 100 μg/ml. Interestingly, the chelators, and especially the aminopolycarboxylic acids retained stabilizing effect despite the relatively low pH favoring protonated forms of the chelators.

It should further be appreciated that contemplated compositions are substantially free of antioxidants (i.e., do not include antioxidants in an amount effective to reduce degradation of total norepinephrine by at least 2% when stored over a period of at least six months at 25° C. Indeed, the inventors discovered that some formulations with antioxidants (particularly with sodium metabisulfite) had decreased stability resulting in more degradation of total norepinephrine by at least 3%. Notably, contemplated formulations were stable as described in more detail below, even in the absence of effective quantities of antioxidants, especially where deoxygenated solvents (e.g., typically water and/or buffer) were employed. Deoxygenation (i.e., reduction of molecular dissolved oxygen) can be achieved in numerous manners, including sparging with inert gases (e.g., helium, various freons, argon, xenon), agitation under vacuum, and/or using enzymatic systems that deplete a solution of dissolved oxygen (see e.g., U.S. Pat. No. 9,187,779). Additionally, or alternatively, ingress of molecular oxygen into the formulation can also be reduced by co-packaging a container with the formulation in a secondary container that includes an oxygen scavenger, and especially a metal-free oxygen scavenger (e.g., GLS100, Ageless®, Pharmakeep®, all commercially available from Mitsubishi Gas Chemical America).

The norepinephrine for preparation of contemplated formulations is preferably (R)-norepinephrine, or enantiomerically pure (i.e., at least 98% R-isomer) norepinephrine. However, in less preferred aspects, isomeric purity can also be between 95-98%, or even between 90-95%. As described herein, it should also be appreciated that the norepinephrine may be a salt of any suitable and pharmaceutically acceptable form, including mineral salts (e.g., HCl salt) and organic salts (e.g., bitartrate). Similarly, where desired, the norepinephrine may also be used in any suitable prodrug form (e.g., β,3-dihydroxytyrosine, L-dihydroxyphenylserine, etc.).

The parenteral formulations of the present application may be sterilized. Non-limiting examples of sterilization techniques include filtration through a bacterial-retaining filter, terminal sterilization, incorporation of sterilizing agents, irradiation and heating. With respect to the sterilization of contemplated formulations it should be appreciated that contemplated formulations may be sterilized using all known manners of sterilization, including filtration through 0.22 micron filters, heat sterilization, autoclaving, radiation (e.g., gamma, electron beam, microwave).

The formulations contemplated herein can also be filtered through a 0.22 micron filter, and filled in amber glass vials, but can also be filled in a polyethylene, polypropylene or low-density polyethylene containers in a blow-fill-seal (BFS) process. BFS is a form of advanced aseptic manufacturing wherein the container is formed, filled, and sealed in one continuous, automated system not requiring human intervention. The process begins with the extrusion of plastic granules in the form of a hot hollow pipe of molten plastic called a parison.

The route of administration may be parenteral or oral, including intravenous, subcutaneous, intra-arterial, intraperitoneal, ophthalmic, intramuscular, rectal, vaginal, intraorbital, intracerebral, intradermal, intracisternal, intracapsular, intraspinal, epidural, intrapulmonary, intranasal, transmucosal, transdermal, via inhalation or buccal.

In certain non-limiting embodiments, the pharmaceutical composition of the present application comprises norepinephrine or a pharmaceutically acceptable salt thereof at a concentration of between about 0.005 µg/ml and about 15 µg/ml, and sodium chloride (NaCl) at a concentration of between about 0.01 and about 2.0 weight percent. In other non-limiting examples, sodium chloride is at a concentration of between about 0.5 to about 20 mg/ml. In other non-limiting examples, sodium chloride is at a concentration of between about 7 to about 12 mg/ml. In other non-limiting embodiments, the norepinephrine composition of the present application comprises norepinephrine or a pharmaceutically acceptable salt thereof at a concentration of about 1 mg/ml and sodium chloride at a concentration of about 0.8 weight percent.

In certain embodiments, the stable injectable norepinephrine solution is further diluted with a solution to provide a final infusion solution comprising from about 1 to about 68 milligrams of norepinephrine. Preferably, that solution used for dilution contains dextrose. In still other embodiments, the final infusion solution comprises 4 micrograms to about 68 micrograms of norepinephrine per liter of dextrose or dextrose/sodium chloride solutions.

In certain non-limiting embodiments, the pharmaceutical composition or norepinephrine solution is disposed in a sealed glass container or vessel that can maintain the sterility of, or prevent the contamination of, norepinephrine composition that is purified or substantially free of contaminants. A container that would be impervious to light and air-tight so as not to permeate oxygen. These may include but not limited to glass vials, glass syringes, plastic vials, plastic syringes, or other types of containers.

Volume of Container

The contemplated vials and their respective fill volumes are presented below:

| Presentation | Volume of Drug |
|---|---|
| 4 mL (4R) | 4 ± 0.30 mL |
| 8 mL (10R) | 8 ± 0.50 mL |
| 16 mL (20R) | 16 ± 0.60 mL |

At minimum, the vial will be made of a material that is non-permeable to air and offers light protection from a wavelength that promotes photo-initiated degradation. Light protection maybe achieved by use of amber vials or a combination of clear vials and a secondary container which could be a cardboard, aluminum-based, plastic or otherwise.

In other non-limiting embodiments, the application provides containers and closure systems suitable for storing norepinephrine formulations of the present application which are aseptically filled. The primary polymeric materials which may be used include, but are not limited to, polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer, etc. which have been demonstrated to be impervious to light and air.

In certain non-limiting embodiments, norepinephrine solutions or pharmaceutical compositions may be stored as a liquid in an aliquot having a total volume between about 0.1 and 100 ml, or between about 0.1 and 10 ml, or between about 0.1 and 5 ml, or between about 0.1 and 2.5 ml, or between about 0.5 ml and 2.5 ml, or between about 0.5 ml and 10 ml, or between about 1 ml and 100 ml, or between about 1 and 10 ml.

In certain non-limiting embodiments, norepinephrine compositions may be stored as a liquid in an aliquot having a total volume of about 2 ml. In certain non-limiting embodiments, norepinephrine compositions may be stored as a liquid in an aliquot having a total volume of about 5 ml. In certain non-limiting embodiments, norepinephrine compositions may be stored as a liquid in an aliquot having a total volume of about 10 ml. In certain non-limiting embodiments, norepinephrine compositions may be stored as a liquid in an aliquot having a total volume of about 20 ml.

In certain non-limiting embodiment, the present application provides for norepinephrine formulations that can be administered for any condition requiring, for example, an increase in blood pressure, including but not limited to: during cardiopulmonary resuscitation (CPR), the treatment of cardiac arrest, profound hypotension. The norepinephrine formulations can also be used for blood pressure control in certain acute hypotensive states, including for example sympathectomy, poliomyelitis, pheochromocytomectomy, spinal anesthesia, myocardial infarction, blood transfusion, and septicemia.

The following examples are offered by way of illustration and not limitation.

EXAMPLES

Example 1

Antioxidant Free Norepinephrine Bitartrate Formulation

Tables 1 shows the formulation composition for a norepinephrine bitartrate formulation which is packaged in 4R (4 mL fill), 10R (8 ml fill) and 20R (16 mL fill) vials.

TABLE 1

| Ingredient | Function | 4 mg/4 mL (4R Vial) | 8 mg/8 mL (10R Vial) | 16 mg/16 mL (20R Vial) |
|---|---|---|---|---|
| Norepinephrine Bitartrate, molecule USP# | Active | 4 mg | 8 mg | 16 mg |
| Sodium Chloride, NF | Tonicity Agent | 32 mg | 64 mg | 128 mg |
| Water for Injection, USP | Vehicle | QS to 4 mL | QS to 8 mL | QS to 16 mL |
| Nitrogen gas, NF | Processing Aid | For Headspace | For Headspace | For Headspace |

The following examples demonstrate that norepinephrine bitartrate formulations of the current invention: 1) have significantly lower impurities, resulting in more pure product; 2) are expected to maintain potency until product expiration, for example at 24 months at room temperature based on extrapolated 40° C. accelerated stability data; and does not contain any sulfur/sulfites making them safe for the general patient population including those prone to sulfur-induced allergies.

For all the Tables below: NR—Not Recorded; NA—Not Applicable; ND—Not Detected; <RT—below reporting threshold

Example 2

Stability

Stability data excerpts of Norepinephrine Bitartrate Injection, USP 1 mg/mL (antioxidant-free) dispensed in three proposed presentations, i.e. 4R, 10R and 20R vials are shown below. The assay, pH, isomer content, and total impurities comparison data shown below is based on the formulation that is charged and maintained at 1% O$_2$ headspace level.

The samples were maintained at long-term storage condition (25±2° C./60±5% RH), intermediate storage temperature (30±2° C./65±5% RH) and accelerated temperature (40±2° C./75±5% RH) for one month (1M), 3 months (3M) and 6 months (6M).

TABLE 2

Norepinephrine Bitartrate Injection, USP
1 mg/mL pH Comparison in the Volumes Disclosed

| Time Point | 4 mL | 8 mL | 16 mL |
|---|---|---|---|
| | Specification: (3.0-4.5) | | |
| T = 0 | 3.45 | 3.47 | 3.44 |
| 1 Month; 25 ± 2° C./60 ± 5% RH - INV | 3.42 | 3.44 | 3.42 |
| 3 Month; 25 ± 2° C./60 ± 5% RH - INV | 3.46 | 3.43 | 3.45 |
| 6 Month; 25 ± 2° C./60 ± 5% RH - INV | 3.45 | 3.42 | 3.48 |
| 6 Month; 25 ± 2° C./60 ± 5% RH - UP | NR | 3.43 | 3.47 |
| 1 Month; 30 ± 2° C./65 ± 5% RH - INV | 3.42 | 3.42 | 3.42 |
| 3 Month; 30 ± 2° C./65 ± 5% RH - INV | 3.46 | 3.45 | 3.45 |
| 6 Month; 30 ± 2° C./65 ± 5% RH - INV | 3.46 | 3.41 | 3.47 |
| 6 Month; 30 ± 2° C./65 ± 5% RH - UP | NR | 3.39 | 3.47 |

TABLE 2-continued

Norepinephrine Bitartrate Injection, USP
1 mg/mL pH Comparison in the Volumes Disclosed

| Time Point | 4 mL | 8 mL | 16 mL |
|---|---|---|---|
| | Specification: (3.0-4.5) | | |
| 1 Month; 40 ± 2° C./75 ± 5% RH - INV | 3.48 | 3.43 | 3.45 |
| 3 Month; 40 ± 2° C./75 ± 5% RH - INV | 3.51 | 3.51 | 3.47 |
| 6 Month; 40 ± 2° C./75 ± 5% RH - INV | 3.47 | 3.40 | 3.47 |
| 6 Month; 40 ± 2° C./75 ± 5% RH - UP | NR | 3.41 | 3.46 |

RH: Relative Humidity;
INV: Inverted Samples;
UP: Upright Samples;
NR: Not Recorded.

The results demonstrate that the proposed antioxidant-free formulation is stable within the pH range of 3.0-4.5 in all stability conditions.

TABLE 3

Norepinephrine Bitartrate Injection, USP
1 mg/mL Assay Comparison in the the Three Presentations

| Time Point | 4 mL | 8 mL | 16 mL |
|---|---|---|---|
| | Specification: (90.0-110.0%) | | |
| T = 0 | 99.8 | 100.0 | 99.8 |
| 1 Month; 25 ± 2° C./60 ± 5% RH - INV | 100.1 | 99.8 | 99.5 |
| 3 Month; 25 ± 2° C./60 ± 5% RH - INV | 98.9 | 99.4 | 99.9 |
| 6 Month; 25 ± 2° C./60 ± 5% RH - INV | 98.1 | 99.3 | 98.1 |
| 6 Month; 25 ± 2° C./60 ± 5% RH - UP | NR | 99.2 | 98.5 |
| 1 Month; 30 ± 2° C./65 ± 5% RH - INV | NR | 102.0 | 99.6 |
| 3 Month; 30 ± 2° C./65 ± 5% RH - INV | 99.5 | 98.9 | 100.2 |
| 6 Month; 30 ± 2° C./65 ± 5% RH - INV | 97.6 | 99.4 | 97.6 |
| 6 Month; 30 ± 2° C./65 ± 5% RH - UP | NR | 98.9 | 98.0 |
| 1 Month; 40 ± 2° C./75 ± 5% RH - INV | 99.6 | 101.6 | 99.7 |
| 3 Month; 40 ± 2° C./75 ± 5% RH - INV | 98.9 | 98.0 | 98.9 |
| 6 Month; 40 ± 2° C./75 ± 5% RH - INV | 94.4 | 97.3 | 95.1 |
| 6 Month; 40 ± 2° C./75 ± 5% RH - UP | NR | 97.7 | 94.7 |

RH: Relative Humidity;
INV: Inverted Samples;
UP: Upright Samples;
NR: Not Recorded.

The DP assay specification is 90-110%. The DP assay is therefore conclusively stable at all temperatures for the proposed antioxidant-free formulation. Noteworthy, the slight differences are attributed to analytically non-confirmed oxygen headspace levels on the 4 and 16 mL fill presentations.

TABLE 4

Norepinephrine Bitartrate Injection, USP
1 mg/mL Isomer Content Comparison in Three Presentations

| Time Point | 4 mL | 8 mL | 16 mL |
|---|---|---|---|
| | Specification (NMT 15%) | | |
| T = 0 | NR | NR | NR |
| 1 Month; 25 ± 2° C./60 ± 5% RH - INV | NR | NR | NR |
| 3 Month; 25 ± 2° C./60 ± 5% RH - INV | 1.86 | 1.38 | 1.90 |
| 6 Month; 25 ± 2° C./60 ± 5% RH - INV | 2.23 | 2.01 | 2.24 |
| 6 Month; 25 ± 2° C./60 ± 5% RH - UP | NR | NR | NR |
| 1 Month; 30 ± 2° C./65 ± 5% RH - INV | NR | 0.99 | NR |
| 3 Month; 30 ± 2° C./65 ± 5% RH - INV | 3.00 | 2.42 | 2.96 |
| 6 Month; 30 ± 2° C./65 ± 5% RH - INV | 3.99 | 3.94 | 3.89 |
| 6 Month; 30 ± 2° C./65 ± 5% RH - UP | NR | 3.96 | NR |
| 1 Month; 40 ± 2° C./75 ± 5% RH - INV | NR | 2.48 | NR |
| 3 Month; 40 ± 2° C./75 ± 5% RH - INV | 6.96 | 7.28 | 7.51 |

TABLE 4-continued

Norepinephrine Bitartrate Injection, USP
1 mg/mL Isomer Content Comparison in Three Presentations

| Time Point | 4 mL | 8 mL | 16 mL |
|---|---|---|---|
| | Specification (NMT 15%) | | |
| 6 Month; 40 ± 2° C./75 ± 5% RH - INV | NR | 11.95 | 12.62 |
| 6 Month; 40 ± 2° C./75 ± 5% RH - UP | NR | 12.52 | NR |

RH: Relative Humidity;
INV: Inverted Samples;
UP: Upright Samples;
NR: Not Recorded;
NMT: Not More Than.

The data shows that the antioxidant-free formulations' isomer content is temperature dependent. When maintained at the recommended drug product storage, the isomerization is minimal and not expected to exceed 7.5% at the time of expiry (long term storage conditions.

TABLE 5

Norepinephrine Bitartrate Injection, USP
1 mg/mL Total ImpuritiesC omparison in the Three
Presentations maintained at about 1% Headspace

| Time Point | 4 mL | 8 mL | 16 mL |
|---|---|---|---|
| | Specification (NMT 3.0%) | | |
| T = 0 | 0.00 | 0.07 | 0.00 |
| 1 Month; 25 ± 2° C./60 ± 5% RH - INV | 0.00 | 0.00 | 0.00 |
| 3 Month; 25 ± 2° C./60 ± 5% RH - INV | 0.00 | 0.13 | 0.00 |
| 6 Month; 25 ± 2° C./60 ± 5% RH - INV | 0.00 | 0.00 | 0.00 |
| 6 Month; 25 ± 2° C./60 ± 5% RH - UP | 0.00 | 0.09 | 0.00 |
| 1 Month; 30 ± 2° C./65 ± 5% RH - INV | 0.00 | 0.00 | 0.00 |
| 3 Month; 30 ± 2° C./65 ± 5% RH - INV | 0.00 | 0.27 | 0.00 |
| 6 Month; 30 ± 2° C./65 ± 5% RH - INV | 0.33 | 0.30 | 0.19 |
| 6 Month; 30 ± 2° C./65 ± 5% RH - UP | NR | 0.00 | 0.14 |
| 1 Month; 40 ± 2° C./75 ± 5% RH - INV | 0.00 | 0.00 | 0.00 |
| 3 Month; 40 ± 2° C./75 ± 5% RH - INV | 0.69 | 0.95 | 0.46 |
| 6 Month; 40 ± 2° C./75 ± 5% RH - INV | 2.34 | 2.15 | 2.07 |
| 6 Month; 40 ± 2° C./75 ± 5% RH - UP | NR | 1.79 | 2.27 |

RH: Relative Humidity;
RRT: Relative Retention Time;
INV: Inverted Samples;
UP: Upright Samples;
NMT: Not More Than Example 3

Norepinephrine Bitartrate Injection, USP 1 mg/mL (Antioxidant-free Formulation) comparison with Claris® (Baxter's antioxidant-free ampoule drug product).

TABLE 6

Comparison of Claris ® (Baxter) with the Current Invention's Antioxidant-Free Formulation.

| Formulation Identification | Time point | Assay | Ismer % | RRT 0.33 | RRT 0.38 | RRT 0.51 | RRT 0.55 | RRT 0.96 | RRT 1.23 | RRT 1.86 | Total (%) |
|---|---|---|---|---|---|---|---|---|---|---|---|
| Current Invention Formulation | Initial | 100.0 | NR | ND | ND | ND | ND | ND | ND | ND | 0.00 |
| Claris ®, 13M sample | | 100.5 | 9.51 | ND | ND | ND | ND | ND | ND | <RT | 0.00 |
| Current Invention Formulation | 1M, 25 ± 2°C./ 60 ± 5% | 99.5 | 1.43 | ND | ND | ND | ND | ND | ND | ND | 0.00 |
| Claris ® | RH | 99.6 | 9.89 | ND | ND | ND | ND | ND | ND | 0.05 | 0.05 |
| Current Invention Formulation | 3M, 30 ± 2° C./65 ± 5% RH | 99.2 | 2.43 | ND | ND | ND | ND | 0.05 | ND | ND | 0.05 |
| Claris ® | | 99.7 | 10.6 | ND | ND | ND | ND | ND | ND | 0.05 | 0.05 |
| Current Invention Formulation | 3M, 40 ± 2° C./75 ± 5% RH | 98.5 | 7.05 | ND | ND | 0.08 | 0.09 | 0.23 | 0.13 | ND | 0.53 |
| Claris ® | | 99.8 | 13.9 | 0.05 | 0.05 | ND | ND | ND | ND | ND | 0.10 |

ND: Not Detected;
RH: Relative Humidity;
RRT: Relative Retention Time;
INV: Inverted Samples;
UP: Upright Samples;
<RT: Less than Reporting Threshold

TABLE 7

Comparison of Levophed ® (18M RLD; with antioxidant) with Claris ® (13M Generic; Baxter) and the Current Invention's antioxidant-free formulations.

| Formulation Identification | Time point | Assay | Ismer % | pH | RRT 0.96 | RRT 1.23 | NSA* RRT 0.20 | RRT 0.82 | Total Imp % |
|---|---|---|---|---|---|---|---|---|---|
| Current Invention Formulation | Initial | 100.0 | NR | 3.46 | ND | ND | NA | NA | 0.00 |
| Claris ® (Baxter) | | 100.5 | 9.51 | 3.49 | ND | ND | | | 0.00 |
| Levophed ® (RLD) | | 97.7 | NR | 3.40 | NA | | 4.71 | ND | |
| Current Invention Formulation | 1M, 25 ± 2° C./60 ± 5% RH | 99.5 | 1.43 | 3.46 | ND | ND | NA | NA | 0.00 |
| Claris ® (Baxter) | | 99.6 | 9.89 | 3.49 | ND | ND | | | 0.05 |
| Levophed ® (RLD) | | 97.6 | 4.51 | 3.42 | NA | | 3.74 | ND | 4.03 |
| Current Invention Formulation | 3M, 40 ± 2° C./75 ± 5% RH | 98.5 | 7.05 | 3.48 | 0.23 | 0.13 | NA | NA | 0.53 |
| Claris ® (Baxter) | | 99.8 | 13.88 | 3.49 | ND | ND | | | 0.10 |
| Levophed ® (RLD) | | 94.1 | 11.9 | 3.39 | NA | | 7.02 | 0.18 | 7.29 |

*NSA Norepinephrine Sulfonic Acid Impurity;
ND: Not Detected;
NR: Not Recorded;
NA: Not Applicable;
RH: Relative Humidity;
RRT: Relative Retention Time The data shows assay, pH, isomer and two main impurities from each formulation. From the stability results of up to three months, drug product formulations of the current invention and Claris® (antioxidant-free formulations) have comparable stability profiles.

In comparison to the RLD which contains sodium metabisulfite antioxidant, formulations of the current invention and Baxter's Claris® formulations portray better assay and lower total impurities.

Example 4

Norepinephrine Bitartrate Injection, USP 1 mg/mL Formulation in a 10R vial (8 mL-fill): Assay, Isomer, pH and Major Impurities Stability Data Comparison at all O2 Headspace levels.

TABLE 9

Comparison of Oxygen Headspace Effect in the Norepinephrine Bitartrate Injection, USP 1 mg/mL (antioxidant-free formulation).

| Time Point | 0.5% HS | 1% HS | 2% HS |
|---|---|---|---|
| pH Specification: (3.0-4.5) | | | |
| T = 0 | 3.47 | 3.47 | 3.47 |
| 1 Month; 25 ± 2° C./60 ± 5% RH - INV | 3.45 | 3.44 | 3.43 |
| 3 Month; 25 ± 2° C./60 ± 5% RH - INV | 3.42 | 3.43 | 3.46 |
| 6 Month; 25 ± 2° C./60 ± 5% RH - INV | 3.43 | 3.42 | 3.41 |
| 6 Month; 25 ± 2° C./60 ± 5% RH - UP | 3.44 | 3.43 | 3.44 |
| 1 Month; 30 ± 2° C./65 ± 5% RH - INV | 3.46 | 3.42 | 3.45 |
| 3 Month; 30 ± 2° C./65 ± 5% RH - INV | 3.45 | 3.45 | 3.42 |
| 6 Month; 30 ± 2° C./65 ± 5% RH - INV | 3.39 | 3.41 | 3.38 |
| 6 Month; 30 ± 2° C./65 ± 5% RH - UP | 3.39 | 3.39 | 3.39 |
| 1 Month; 40 ± 2° C./75 ± 5% RH - INV | 3.44 | 3.43 | 3.42 |
| 3 Month; 40 ± 2° C./75 ± 5% RH - INV | 3.45 | 3.51 | 3.43 |
| 6 Month; 40 ± 2° C./75 ± 5% RH - INV | 3.48 | 3.40 | 3.44 |
| 6 Month; 40 ± 2° C./75 ± 5% RH - UP | 3.46 | 3.41 | 3.39 |
| Assay Analysis (Units: % LC, Specification: 90.0-110.0%) | | | |
| T = 0 | 100.0 | 100.0 | 100.0 |
| 1 Month; 25 ± 2° C./60 ± 5% RH - INV | 100.2 | 99.8 | 99.9 |
| 3 Month; 25 ± 2° C./60 ± 5% RH - INV | 99.5 | 99.4 | 98.8 |
| 6 Month; 25 ± 2° C./60 ± 5% RH - INV | 99.4 | 99.3 | 99.0 |
| 6 Month; 25 ± 2° C./60 ± 5% RH - UP | 99.4 | 99.2 | 99.9 |
| 1 Month; 30 ± 2° C./65 ± 5% RH - INV | 101.7 | 102.0 | 101.4 |
| 3 Month; 30 ± 2° C./65 ± 5% RH - INV | 99.2 | 98.9 | 99.1 |
| 6 Month; 30 ± 2° C./65 ± 5% RH - INV | 99.0 | 99.4 | 98.3 |
| 6 Month; 30 ± 2° C./65 ± 5% RH - UP | 99.5 | 98.9 | 99.1 |
| 1 Month; 40 ± 2° C./75 ± 5% RH - INV | 101.6 | 101.6 | 101.0 |
| 3 Month; 40 ± 2° C./75 ± 5% RH - INV | 98.5 | 98.0 | 97.2 |
| 6 Month; 40 ± 2° C./75 ± 5% RH - INV | 97.6 | 97.3 | 95.6 |
| 6 Month; 40 ± 2° C./75 ± 5% RH - UP | 98.0 | 97.7 | 95.7 |
| Isomer Content Analysis (Units: %, Specification: Not More Than 15%) | | | |
| T = 0 | NR | NR | NR |
| 1 Month; 25 ± 2° C./60 ± 5% RH - INV | NR | NR | NR |
| 3 Month; 25 ± 2° C./60 ± 5% RH - INV | 1.43 | 1.38 | 1.41 |
| 6 Month; 25 ± 2° C./60 ± 5% RH - INV | 2.00 | 2.01 | NR |
| 6 Month; 25 ± 2° C./60 ± 5% RH - UP | 2.00 | NR | 2.03 |
| 1 Month; 30 ± 2° C./65 ± 5% RH - INV | 1.00 | 0.99 | 1.00 |
| 3 Month; 30 ± 2° C./65 ± 5% RH - INV | 2.43 | 2.42 | 2.39 |
| 6 Month; 30 ± 2° C./65 ± 5% RH - INV | 3.71 | 3.94 | 3.99 |
| 6 Month; 30 ± 2° C./65 ± 5% RH - UP | 3.87 | 3.96 | 3.99 |
| 1 Month; 40 ± 2° C./75 ± 5% RH - INV | 2.47 | 2.48 | 2.50 |
| 3 Month; 40 ± 2° C./75 ± 5% RH - INV | 7.05 | 7.28 | 6.66 |
| 6 Month; 40 ± 2° C./75 ± 5% RH - INV | NR | 11.95 | 12.04 |
| 6 Month; 40 ± 2° C./75 ± 5% RH - UP | 12.54 | 12.52 | 12.66 |
| Total Impurities (Units: %, Specification: NMT 2.0%) | | | |
| T = 0 | 0.07 | 0.07 | 0.07 |
| 1 Month; 40 ± 2° C./75 ± 5% RH - INV | 0.00 | 0.00 | 0.00 |
| 3 Month; 40 ± 2° C./75 ± 5% RH - INV | 0.64 | 0.95 | 1.57 |
| 6 Month; 40 ± 2° C./75 ± 5% RH - INV | 1.92 | 2.15 | 3.48 |
| 6 Month; 40 ± 2° C./75 ± 5% RH - UP | 1.86 | 1.79 | 3.57 |

NR: Not Recorded;
RH: Relative Humidity;
INV: Inverted Samples;
UP: Upright Samples;
NMT: Not More Than.

The data shows that oxygen headspace control plays a significant role in stabilizing the proposed antioxidant-free formulations.

Although the foregoing invention has been described in some detail by way of illustration and example for purposes of clarity of understanding, it will be obvious that certain changes and modifications may be practiced within the scope of the claims.

We claim:

1. A stable injectable norepinephrine solution in a glass vial comprising: norepinephrine or a pharmaceutically acceptable salt thereof in an amount from
about 0.5 to about 1.5 mg/mL; sodium chloride;
a pharmaceutically acceptable carrier comprising water;
headspace oxygen that is from about 0% v/v to about 10.0% v/v from the time of manufacture to about 24 months from manufacture when stored at room temperature;
wherein the solution is free of preservatives and antioxidants; and, wherein the fill volume of the glass vial is from about 2 to about 20 mL.

2. The stable injectable norepinephrine solution of claim 1, wherein norepinephrine or a pharmaceutically acceptable salt thereof is present in an amount of 1 mg/mL.

3. The stable injectable norepinephrine solution of claim 1, wherein the solution is free of sulfites.

4. The stable injectable norepinephrine solution of claim 1, wherein the solution is further diluted with dextrose-containing solutions to provide a final infusion solution comprising from about 1 to about 68 mg of norepinephrine.

5. The stable injectable norepinephrine solution of claim 4, wherein the final infusion solution comprises 4 micrograms to about 68 micrograms of norepinephrine per mL of dextrose or dextrose/sodium chloride solutions.

6. The stable injectable norepinephrine solution of claim 1 maintained with 0.5% oxygen headspace, wherein any single impurity will be about 0.001 wt % to about 1.0 wt. %, and wherein the total impurities in the formulation are not more than 3.0 wt. %.

7. The stable injectable norepinephrine solution of claim 1 prepared by sparging with inert gases to achieve dissolved oxygen levels of about 0 to about 2 ppm during compounding.

8. The stable injectable norepinephrine solution of claim 1, wherein the dissolved oxygen levels of the solution are present in about 0 to about 5 ppm when measured up to three months or more.

9. The stable injectable norepinephrine solution of claim 1, wherein the resulting pH of the solution is from about 3.0 to about 4.5.

10. The stable injectable norepinephrine solution of claim 1, wherein the oxygen headspace in the vial is from about 0% v/v to about 2% v/v.

11. The stable injectable norepinephrine solution of claim 1, wherein the solution exhibits no more than a 5% decrease in the concentration of norepinephrine when stored in the amber glass vial for at least 24 months at 25° C.

12. The stable injectable norepinephrine solution of claim 1, wherein the fill volume of the glass vial is from 4 to about 16 mL.

13. The stable injectable norepinephrine solution of claim 1, further comprising a chelating agent.

14. The stable injectable norepinephrine solution of claim 13, wherein the chelating agent is a metal ion chelator.

15. The stable injectable norepinephrine solution of claim 14, wherein the metal ion chelator is selected from the group consisting of bicarboxylic acids, tricarboxylic acids, and aminopolycarboxylic acids, and salts and hydrates thereof.

16. The stable injectable norepinephrine solution of claim 1, further comprising a buffer.

17. The stable injectable norepinephrine solution claim 16, wherein the buffer is a one or more of a glycine, citrate, acetate, bicarbonate and phosphate buffer.

18. The stable injectable norepinephrine solution of claim 17, wherein the buffer maintains the pH of the solution from about 3.0 to about 4.5.

19. A stable injectable norepinephrine solution in a glass vial comprising: norepinephrine or a pharmaceutically acceptable salt thereof in an amount of about 1.0 mg/mL;
sodium chloride;
a pharmaceutically acceptable carrier comprising water;
a buffer;
the headspace oxygen that is from about 0% v/v to about 2% v/v from the time of manufacture to about 24 months from manufacture when stored at room temperature;
wherein the solution is free of sulfites; and, wherein the fill volume of the glass vial is from about from 4 to about 16 mL.

20. The stable injectable norepinephrine solution of claim 19, wherein the buffer maintains the pH of the solution from about at 3.0 to about 4.5.

21. The stable injectable norepinephrine solution of claim 15, wherein the aminopolycarboxylic acid is selected from group consisting of ethylenediaminetetraacetic acid (EDTA), ethylene glycol-bis(β-aminoethyl ether)-N,N,N', N'-tetraacetic acid (EGTA), and penta(carboxymethyl)diethylenetriamine (DTPA), and salts and hydrates thereof.

* * * * *